(12) United States Patent
DiNucci

(10) Patent No.: US 8,092,488 B2
(45) Date of Patent: Jan. 10, 2012

(54) BONE RETRACTOR TOOL

(76) Inventor: Kent DiNucci, Omaha, NE (US)

( * ) Notice: Subject to any disclaimer, the term of this patent is extended or adjusted under 35 U.S.C. 154(b) by 364 days.

(21) Appl. No.: 12/004,573

(22) Filed: Dec. 21, 2007

(65) Prior Publication Data

US 2008/0242937 A1    Oct. 2, 2008

Related U.S. Application Data

(60) Provisional application No. 60/920,839, filed on Mar. 30, 2007.

(51) Int. Cl.
*A61B 17/00* (2006.01)
(52) U.S. Cl. ........ 606/205; 606/206; 600/190; 600/196; 600/201; 600/222
(58) Field of Classification Search .......... 600/184–246; 606/205–208, 99, 105, 86 A, 86 B, 90
See application file for complete search history.

(56) References Cited

U.S. PATENT DOCUMENTS 6,565,570 B2 *   5/2003   Sterett et al. ................. 606/280

* cited by examiner

*Primary Examiner* — Eduardo C Robert
*Assistant Examiner* — Christina Negrelli
(74) *Attorney, Agent, or Firm* — Stinson Morrisson Heckler LLP

(57) ABSTRACT

An improved bone retractor tool includes a pair of arms pivotably connected to one in a pliers-like configuration and a pair of tissue engagement plates each having forward and rearward portions, each of the pair of tissue engagement plates mounted on the upper end of one of the pair of arms and extending generally parallel with one another when the pair of arms are in closed position. Forward bone engagement spikes are mounted on and extend forwards from the forward portions of the tissue engagement plates. A releasable securement mechanism is mounted on the pair of arms for releasably retaining the pair of arms in a selected position relative to one another, and a tensioning device is mounted on the pair of arms for tensioning the lower ends away from one another thereby forcing the pair of tissue engagement plates towards one another upon the securement mechanism being released.

18 Claims, 4 Drawing Sheets

BONE RETRACTOR TOOL

CROSS-REFERENCE TO RELATED PATENTS

This application claims priority based on a provisional patent, specifically on the Provisional Patent Application Ser. No. 60/920,839 filed Mar. 30, 2007.

BACKGROUND OF THE INVENTION

1. Technical Field

The present invention is directed to surgical tools and, more particularly, to an improved bone retractor tool which includes a pair of pliers-like arms pivotably connected to one another, a pair of tissue engagement plates each mounted on an upper end of one of the arms and extending generally parallel with one another, the tissue engagement plates each further including forward bone engagement spikes which extend forward from the plates for entering into and being releasably retained within the bone of a person on whom an operation is being performed, a ratcheting securement mechanism mounted on one of the arms for releasably retaining the arms in a selected position relative to one another, and a tensioning device for tensioning the lower ends of the arms away from one another to force the tissue engagement plates towards one another when the ratcheting securement device is released.

2. Description of the Prior Art

Many different surgical procedures require access to the bones being operated upon, such as bone grafts and the like. One such procedure is commonly referred to as the "Evans" procedure, and it is a calcaneal lengthening procedure which requires a transverse bone cut through the distal part of the calcaneus. The bone then must be retracted to insert a graft wedge in the calcaneus to lengthen the lateral column and correct a flat foot. However, it is not simply a matter of accessing the bone and performing the graft, as the tissue and bone surfaces must be retracted to properly perform the operation. In fact, many different retractors have been developed and used but these invariably utilize the idea of inserting some element into the joint to retract the surfaces, which works well initially but then makes it difficult to access the desired surfaces to clean the cartilage off for a competent fusion. Also, a procedure that this gives advantage to is a fusion of two small joints. Impacting the spikes into the bone adjacent to the joint allows the joint to be opened and cleaned out without the retractor being in the way. After the joint is cleaned off, the holes from the spikes can be used for a staple to be inserted for fixation of the fusion or the previous Evans procedure. Basically, current methods and devices render the actual insertion of the graft a more difficult procedure because the retractor itself is in the way.

Therefore, an object of the present invention is to provide an improved bone retractor tool.

Another object of the present invention is to provide an improved bone retractor tool which includes a pliers-like handle and a pair of parallel plates, one mounted on each of the upper ends thereof, such that the plates may be spread apart from one another to open the graft area.

Another object of the present invention is to provide an improved bone retractor tool which, when spread apart, leaves the space between the plates open and unimpeded to facilitate access to the graft area.

Another object of the present invention is to provide an improved bone retractor tool which includes bone engagement spikes on the forward ends of the plates which enter the bone for easier separation of the joint for grafting of the tendon or ligament thereto and then are usable for insertion of a staple or the like therein to secure the bone joint in its original configuration.

Finally, an object of the present invention is to provide improved bone retractor tool which is relatively simple and durable in construction and is safe, efficient and effective in use.

SUMMARY OF THE INVENTION

The present invention provides an improved bone retractor tool which includes a pair of arms pivotably connected to one another intermediate the upper and lower ends thereof, the pair of arms pivotable between an open position and a closed position and a pair of tissue engagement plates each having forward and rearward portions, each of the pair of tissue engagement plates mounted on the upper end of one of the pair of arms and extending generally parallel with one another when the pair of arms are in the closed position. Forward bone engagement spikes are mounted on and extend forwards from the forward portions of the pair of tissue engagement plates. A releasable securement mechanism is mounted on at least one of the pair of arms for releasably retaining the pair of arms in a selected position relative to one another, and a tensioning device is mounted on at least one of the pair of arms for tensioning the lower ends of the pair of arms away from one another thereby forcing the pair of tissue engagement plates towards one another upon the securement mechanism being released.

The present invention thus provides numerous advantages over the prior art. For example, because access between the tissue engagement plates is not impeded by operative structures of the bone retractor tool, it is far easier for the doctor using the present invention to properly and efficiently perform the operation in which the present invention is being used. Furthermore, as the present invention can be releasably secured in many different spaced positions, it can be used for persons of all different sizes and in many different configurations. Finally, because the bone engagement spikes form holes in the bone which are then usable for insertion and retention of securement staples therein, formation of additional holes in the bone for the staples becomes unnecessary and therefore bone damage and trauma is minimized, which therefore renders the present invention a substantial improvement over the prior art.

DESCRIPTION OF THE PREFERRED EMBODIMENT

The bone retractor tool 10 of the present invention is shown best in FIGS. 1-4 as including left and right arms 12 and 14 which are connected to one another at a pivoting joint 16 positioned towards the upper ends 18 and 20 of the left and right arms 12 and 14. It is preferred that the left and right arms 12 and 14 have a similar shape and function as plier arms, with the dimensions of the left and right arms 12 and 14 being approximately six to eight inches in length, and further that they be constructed of stainless steel or the like so that the bone retractor tool 10 may be cleaned in an autoclave device or the like.

Figure 1:
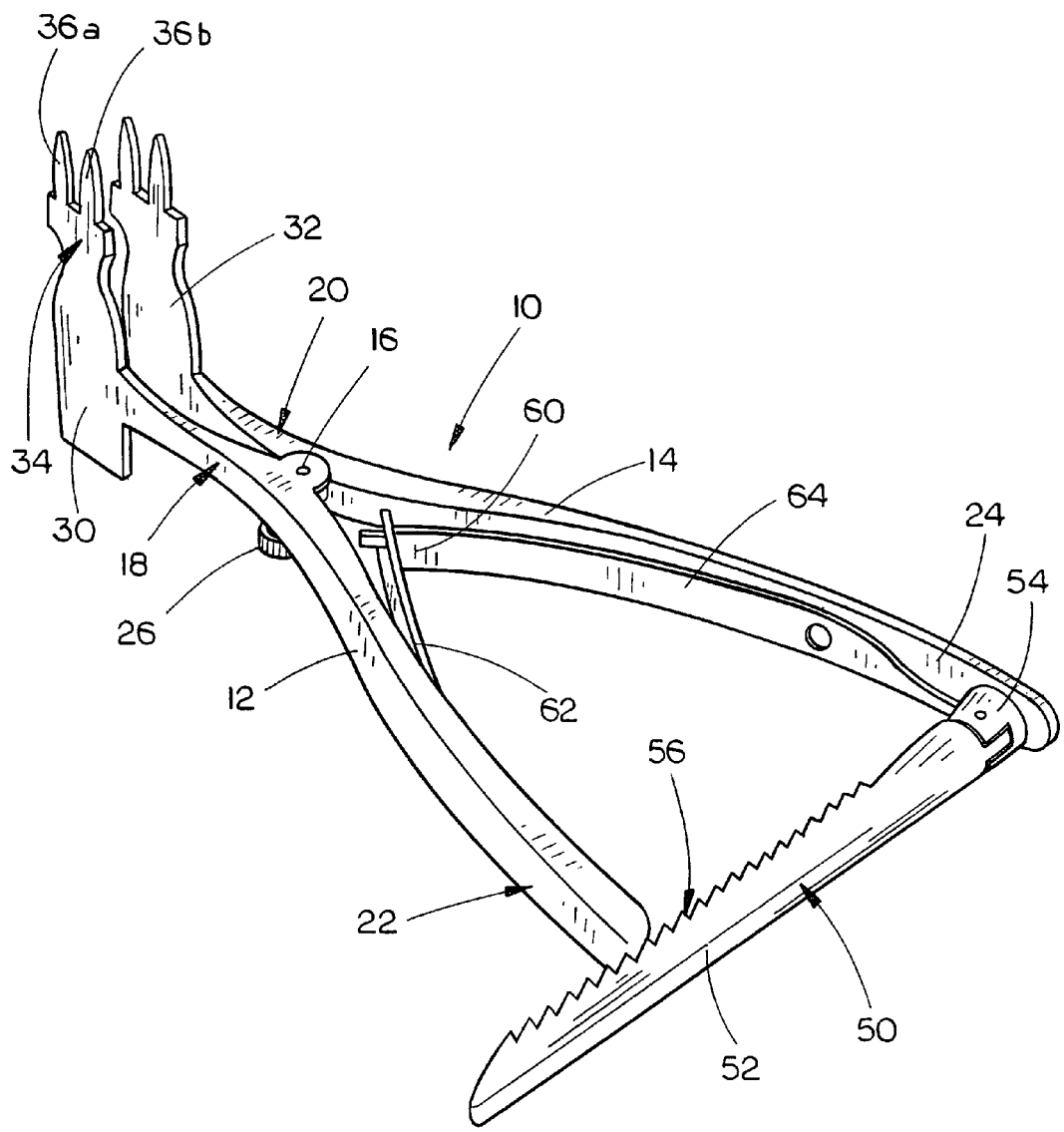
FIG. 1 is a perspective view of the bone retractor tool of the present invention.
Figure 2:
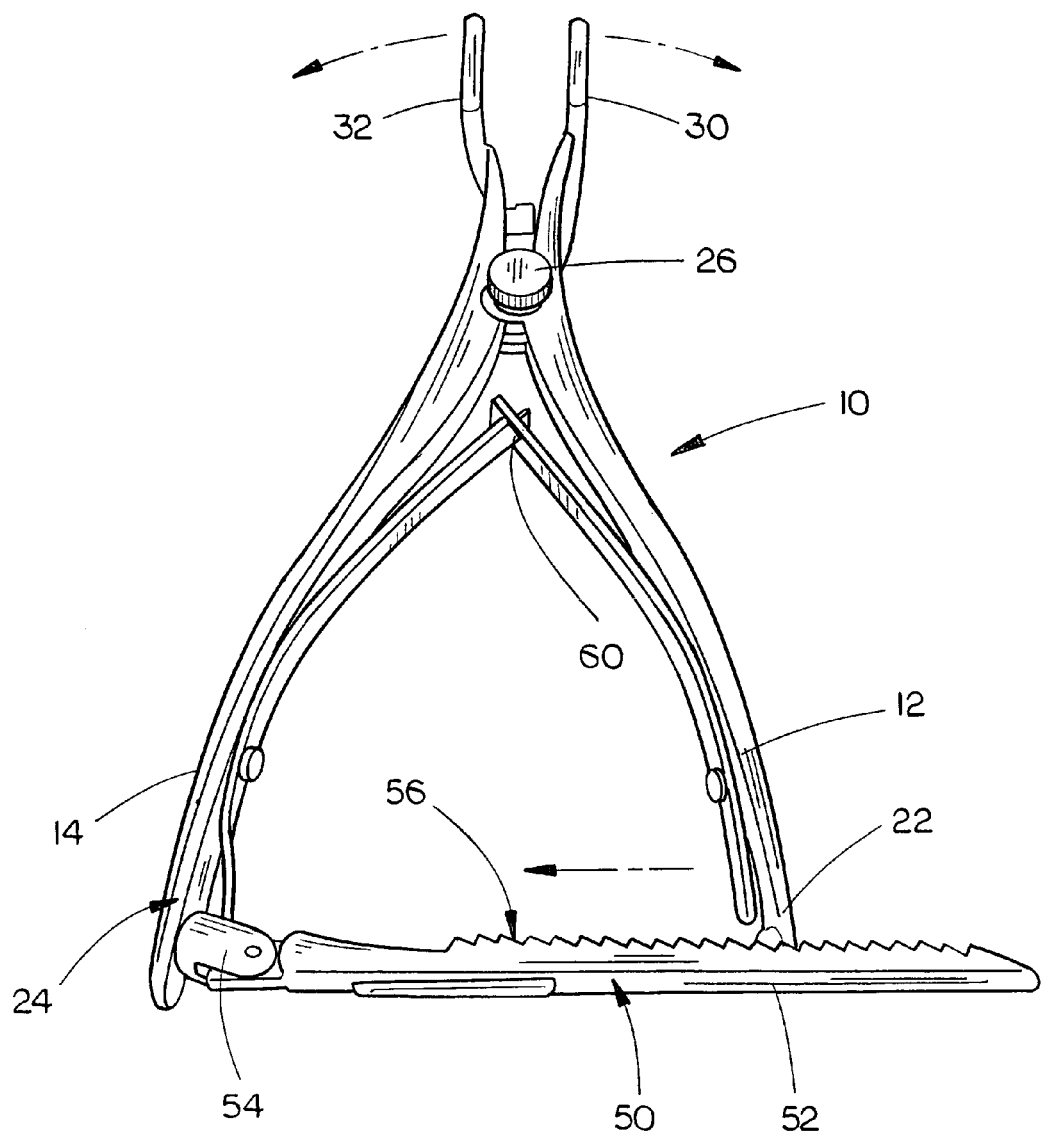
FIG. 2 is a top plan perspective view of the device showing how the movement of the arms coincides with movement of the engagement plates.
Figure 3:
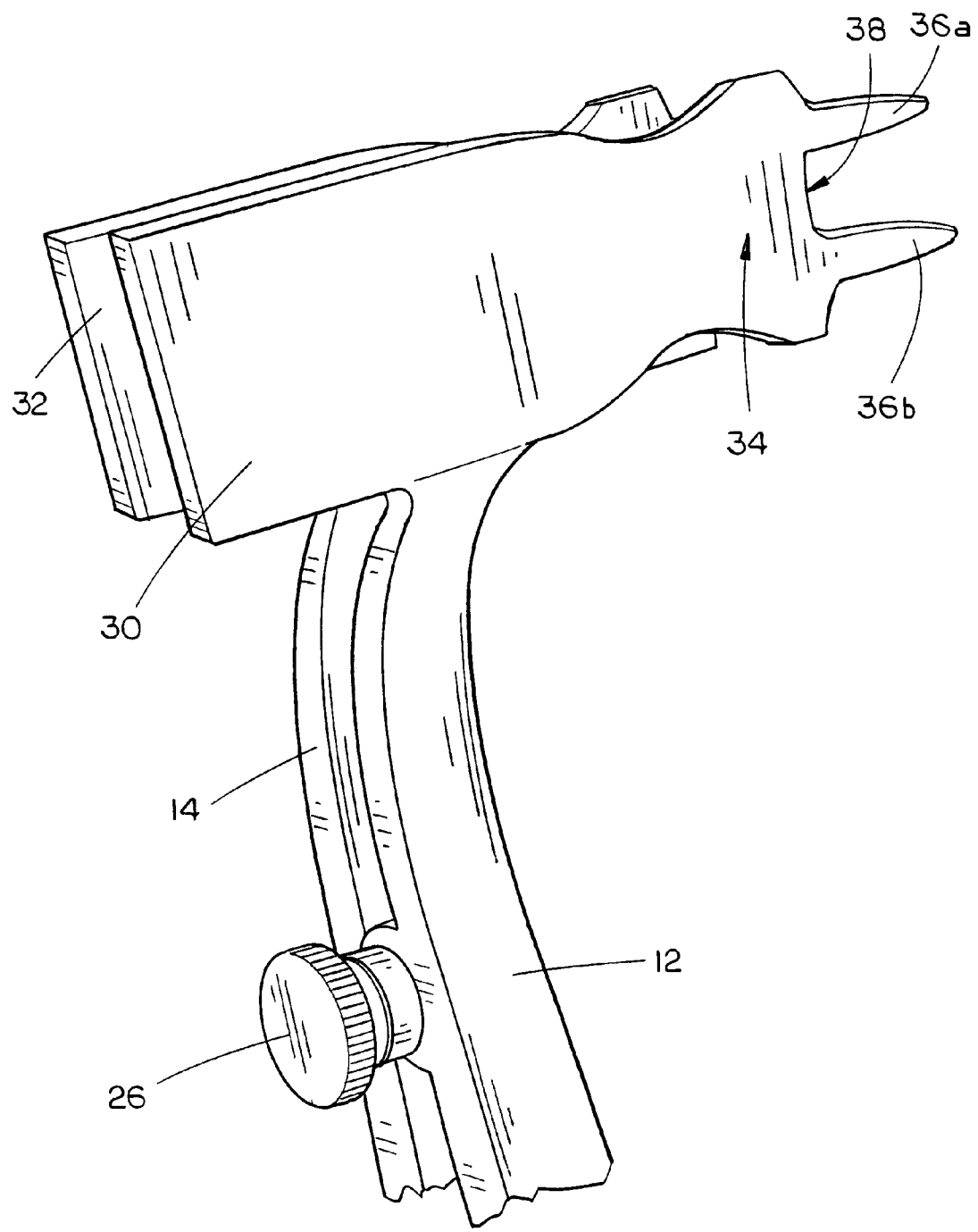
FIG. 3 is a detailed perspective view of the left and right tissue engagement plates of the present invention.
Figure 4:
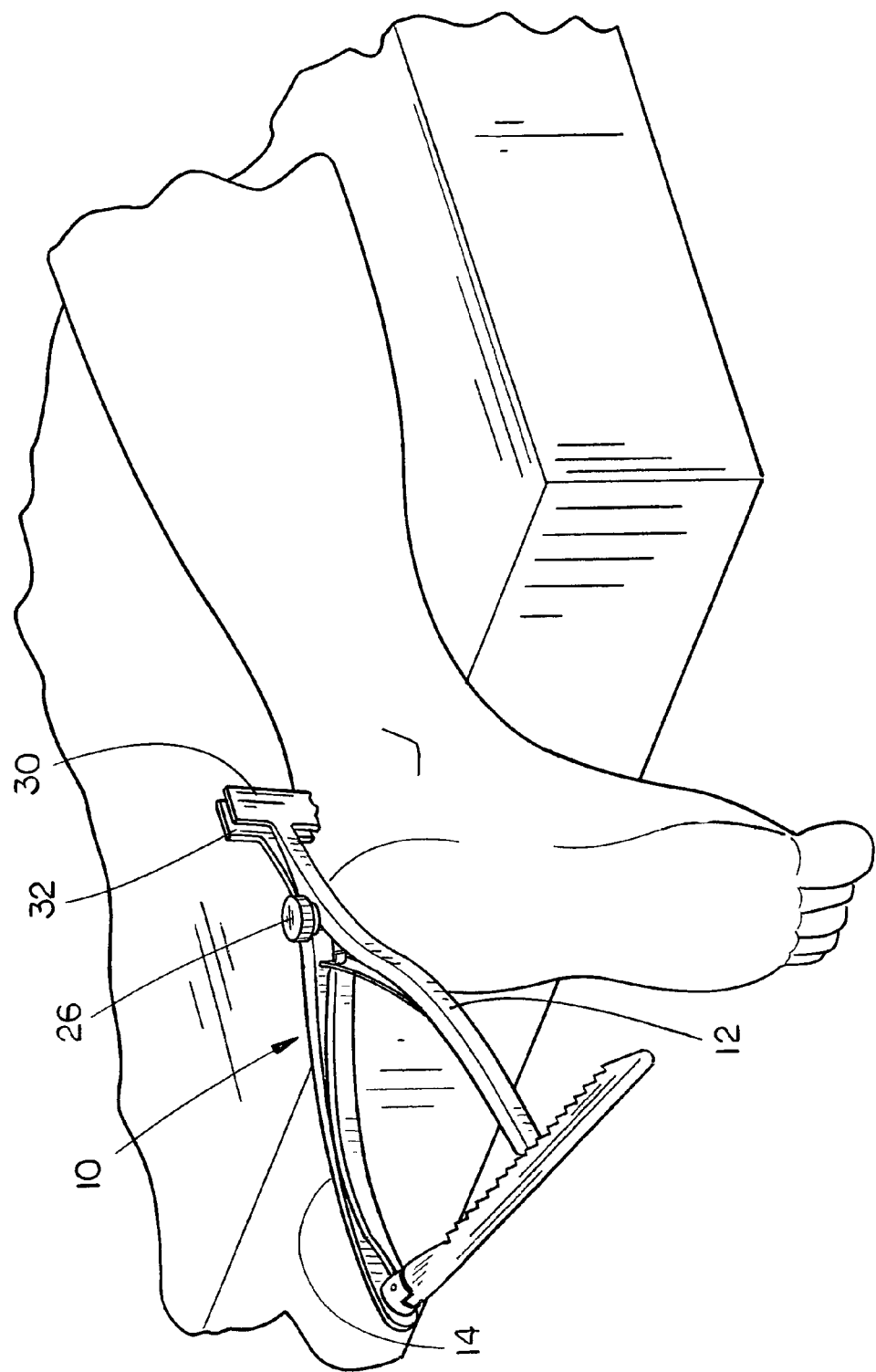
FIG. 4 is a perspective view of the present invention being used to assist in a bone graft.

Mounted on the upper ends 18 and 20 of left and right arms 12 and 14 are left and right tissue engagement plates 30 and 32, as shown best in FIGS. 1-3. In the preferred embodiment, each of the left and right tissue engagement plates 30 and 32 would be generally identical in size, shape and construction materials, and therefore the description of left tissue engagement plate 30 should be understood to apply equally to right tissue engagement plate 32. In the preferred embodiment, left tissue engagement plate 30 would be generally rectangular in shape and have dimensions of approximately three quarters of an inch to one-half inches in length and one-half to one inch in height, with the forward end 34 of left tissue engagement plate 30 further including a pair of forwardly-extending bone engagement spikes 36a and 36b. The bone engagement spikes 36a and 36b would each extend forward from the forward end 34 of left tissue engagement plate 30 and would be approximately one quarter to three quarters of an inch in length and further would be generally flat and in parallel alignment with the left tissue engagement plate 30 yet which would also include a pointed side configuration, as shown best in FIG. 1, such that each of the pair of forwardly-extending bone engagement spikes 36a and 36b has a configuration similar to that of a sharpened picket of a picket fence. It is preferred that the bone engagement spikes 36a and 36b be constructed of the same hardened stainless steel metal used to construct left tissue engagement plate 30 so that the bone engagement spikes 36a and 36b are very sturdy and strong and will easily enter into and engage the bone during use of the bone retractor tool 10 of the present invention.

Mounted on the lower end 24 of right arm 14 and extending towards the lower end 22 of left arm 12 is a ratcheting securement device 50 which, in the preferred embodiment, would include a pivotally mounted ratchet arm 52 mounted on a pivot mount base 54 connected to and mounted on the lower end 24 of right arm 14. The ratchet arm 52 extends across and engages the lower end 22 of left arm 12 with the ratchet teeth 56 of ratchet arm 52 selectively engaging the lower end 22 of left arm 12 to retain the left arm 12 in a selected position relative to the right arm 14, as shown best in FIG. 2. The ratchet arm 52 would be disengaged from the lower end 22 of left arm 12 by pivoting the ratchet arm 52 downwards on pivot mount base 54 to disengage the ratchet teeth 56 from the lower end 22 of left arm 12. The left arm and right arm 12 and 14 may then be pivoted relative to one another about pivoting joint 16 without being releasably retained in a selected position by the ratcheting securement device 50.

Finally, a tension device 60 is provided which extends between and connects the left and right arms 12 and 14 by a pair of tension spring plates 62 and 64 each mounted on one of the left and right arms 12 and 14. The tension device 60 acts to bias the left and right arms 12 and 14, specifically the lower ends 22 and 24 of left and right arms 12 and 14, away from one another thus forcing the left and right tissue engagement plates 30 and 32 into contact with one another, as shown best in FIGS. 2 and 3. Of course, it should be noted that many different types of securement devices 50 and tension devices 60 may be used with the bone retractor tool 10 of the present invention which perform substantially the same functions, and such substitutions would be understood by one skilled in the art.

Also, it may be important to include a securement screw operative to releasably fix the pivoting joint 16 in a selected position, thereby providing two separate means by which the relative positions of left and right arms 12 and 14 may be fixed. The securement screw 26 would be mounted adjacent pivoting joint 16 and would be operative to tighten the pivoting joint 16 to prevent the pivoting motion of the left and right arms 12 and 14 relative to one another, and by merely untightening the securement screw 26, the pivoting motion of left and right arms 12 and 14 via pivoting joint 16 may be resumed.

In use, the bone retractor tool 10 of the present invention would be inserted into the incision in the tissue above the location where the surgery is taking place, namely in the correct position to operate on the afflicted bone. The insertion begins with the left and right tissue engagement plates 30 and 32 in parallel contact with one another in closed position. The closed position is where the plates are approximately 1 cm apart from each other to place the osteotomy/bone cut or joint in between the plates. The forward portions of the left and right tissue engagement plates 30 and 32 are slid into the incision and the bone engagement spikes 36a and 36b on the left and right tissue engagement plates 30 and 32 are then tamped into the two adjacent bones (i.e. a joint) or into the ends of a cut bone approximately one-fourth of an inch, the arms are pushed together and the plates will distract the bone therein so that the bone graft may be inserted. It should be noted that it is generally preferred that the bone retractor tool 10 of the present invention be used with small joints, although it may be possible to use the invention with larger joints should the need arise. Once the bone engagement spikes 36a and 36b are inserted into the bone, the lower ends 22 and 24 of the left and right arms 12 and 14 are moved towards one another thus pivoting the left and right arms 12 and 14 about the pivoting joint 16 such that the left and right tissue engagement plates 30 and 32 and hence bone engagement spikes 36a and 36b move away from one another. The joint or cut bone will be distracted, thus opening access to the procedure location, and due to the configuration of the present invention, there is nothing between the left and right tissue engagement plates 30 and 32 and thus the inside of the bone and/or joint is fully exposed to allow unimpeded access to the bone. Also, as the left and right tissue engagement plates 30 and 32 are within the incision and the bone, the surrounding tissue and skin on the outer sides of the left and right tissue engagement plates 30 and 32 is pushed outwards, and due to the elasticity of the skin and tissue, the incision is widened without causing further damage to the skin and tissue. The incision is thus opened to provide access to the repair area and because the left and right tissue engagement plates 30 and 32 do not have any structure extending directly between them, there is nothing to interfere with access to the bone area being operated upon, unlike those devices found in the prior art.

Once the incision is opened the desired amount, the left and right arms 12 and 14 are secured in the selected positions by engagement of the securement screw 26 on the pivoting joint 16 or, preferably, by engagement of the ratcheting securement device 50 to secure the left and right arms 12 and 14 in the selected position. It is important to note that because the bone engagement spikes 36a and 36b are generally flat with a pointed side configuration, they engage substantially more bone surface thereby generally preventing the spikes from slicing through the bone as you retract, as is often encountered in using cylindrical spikes found in the prior art. This added feature allows the improved retractor of the present invention to be used in softer bone and obtain a better fusion site without creating as much damage to the adjacent bone. Also, the base of each of the left and right tissue engagement plates 30 and 32 from which the bone engagement spikes 36a and 36b extend forms a bone penetration stop face 38 which prevents the bone engagement spikes 36a and 36b from being over-inserted, thus preventing unintentional damage to the bone being operated upon.

Once the operation is completed, the bone retractor tool 10 is removed by releasing the securement screw 26 on the pivoting joint 16 or the ratcheting securement device 50, pivoting the left and right arms 12 and 14 about the pivoting joint 16 to bring the left and right tissue engagement plates 30 and 32 towards one another, shifting the tool back and forth to release the bone engagement spikes 36a and 36b from the bone, then removing the left and right tissue engagement plates 30 and 32 from the incision by lifting them out of the incision. The bone or bones return to their pre-retracted state, and the surgeon or nurse may then put a staple across the joint/bone which utilizes the same holes that were formed by insertion of the bone engagement spikes 36a and 36b. The operation then can be completed by the surgeon or nurse at their leisure.

It is to be understood that numerous additions, modifications and substitutions may be made to the bone retractor tool 10 of the present invention which fall within the intended broad scope of the above description. For example, the size, shape and construction materials used in connection with the bone retractor tool 10 may be modified or changed so long as the intended functional features are neither degraded nor destroyed. Furthermore, although the present invention has been described as being generally designed for use in connection with bone grafts or other such repairs, it should be noted that the bone retractor tool 10 may be used in many other types of operations as will be determined through use of the invention. Finally, it should be noted that the operative elements of the bone retractor tool 10 such as the bone engagement spikes 36a and 36b and the left and right tissue engagement plates 30 and 32 may be modified in size and shape depending on the intended usage of the present invention, and such modification would be understood by one skilled in the art of medical equipment and the use thereof.

There has therefore been shown and described a bone retractor tool 10 which accomplishes all of its intended objectives.

I claim:

1. A bone retractor tool for opening access to a joint space or bone cut, comprising:
a pair of arms pivotably connected to one another intermediate the upper and lower ends thereof, said pair of arms pivotable between open and a closed positions;
a pair of tissue engagement plates each having forward and rearward portions, each of said pair of tissue engagement plates mounted on said upper end of one of said pair of arms and extending generally parallel with one another when said pair of arms are in said closed position such that said tissue engagement plates do not contact each other in said open or closed position;
forward bone engagement spikes mounted on and extending forwards from said forward portions of said pair of tissue engagement plates for insertion into the bone outside, on either side of, the joint space or bone cut and opening access thereto when said arms are in the closed position;
a releasable securement mechanism mounted on at least one of said pair of arms for releasably retaining said pair of arms in a selected position relative to one another; and
a tensioning device mounted on at least one of said pair of arms for tensioning said lower ends of said pair of arms away from one another thereby forcing said pair of tissue engagement plates towards one another upon said securement mechanism being released.

2. The bone retractor tool of claim 1 wherein said pair of arms are connected in a pliers configuration.

3. The bone retractor tool of claim 1 wherein each of said pair of tissue engagement plates is generally rectangular in shape and generally planar and further the rearward portions of each of said pair of tissue engagement plates includes a generally straight edge to facilitate striking of said pair of tissue engagement plates to drive said forward bone engagement spikes into bone.

4. The bone retractor tool of claim 3 wherein said forward bone engagement spikes each are generally flat and extend in generally parallel alignment with the one of said pair of tissue engagement plates on which each of said forward bone engagement spike is mounted, each of said forward bone engagement spikes further including a forward point.

5. The bone retractor tool of claim 1 further comprising four forward bone engagement spikes, two mounted on each of said pair of tissue engagement plates.

6. The bone retractor tool of claim 1 wherein said releasable securement mechanism comprises a ratcheting securement device including a pivotally mounted ratchet arm having a plurality of ratchet teeth, said ratchet arm connected to and mounted on said lower end of one of said pair of arms, said ratchet arm operative to extend across and selectively engage with one of said plurality of ratchet teeth thereon said lower end of the other of said pair of arms thereby retaining said pair of arms in a selected relative position.

7. The bone retractor tool of claim 1 wherein said tensioning device comprises a spring tensioning device operative to bias said lower ends of said pair of arms away from one another thus forcing said pair of tissue engagement plates towards and into contact with one another.

8. The bone retractor tool of claim 1 further comprising a securement screw mounted on said pair of arms adjacent the pivoting joint connecting said pair of arms, said securement screw operative to tighten said pivoting joint to generally prevent pivoting motion of said pair of arms relative to one another.

9. A bone retractor tool comprising:
a pair of arms pivotably connected to one another intermediate the upper and lower ends thereof, said pair of arms pivotable between an open position and a closed position;
a pair of tissue engagement plates each having forward and rearward portions, each of said pair of tissue engagement plates being generally rectangular and planar in shape and each mounted on said upper end of one of said pair of arms and extending generally parallel with one another when said pair of arms are in said closed position;
at least two forward bone engagement spikes mounted on and extending forwards from each of said forward portions of said pair of tissue engagement plates;
a releasable securement mechanism mounted on at least one of said pair of arms for releasably retaining said pair of arms in a selected position relative to one another; and
a tensioning device mounted on at least one of said pair of arms for tensioning said lower ends of said pair of arms away from one another thereby forcing said pair of tissue engagement plates towards one another upon said securement mechanism being released.

10. The bone retractor tool of claim 9 wherein said pair of arms are connected in a pliers configuration.

11. The bone retractor tool of claim 9 wherein said forward bone engagement spikes each are generally flat and extend in generally parallel alignment with the one of said pair of tissue engagement plates on which each of said forward bone engagement spike is mounted, each of said forward bone engagement spikes further including a forward point.

12. The bone retractor tool of claim 9 further comprising four forward bone engagement spikes, two mounted on each of said pair of tissue engagement plates.

13. The bone retractor tool of claim 9 wherein said releasable securement mechanism comprises a ratcheting securement device including a pivotally mounted ratchet arm having a plurality of ratchet teeth, said ratchet arm connected to and mounted on said lower end of one of said pair of arms, said ratchet arm operative to extend across and selectively engage with one of said plurality of ratchet teeth thereon said lower end of the other of said pair of arms thereby retaining said pair of arms in a selected relative position.

14. The bone retractor tool of claim 9 wherein said tensioning device comprises a spring tensioning device operative to bias said lower ends of said pair of arms away from one another thus forcing said pair of tissue engagement plates towards and into contact with one another.

15. The bone retractor tool of claim 9 further comprising a securement screw mounted on said pair of arms adjacent the pivoting joint connecting said pair of arms, said securement screw operative to tighten said pivoting joint to generally prevent pivoting motion of said pair of arms relative to one another.

16. The bone retractor tool of claim 9 wherein said rearward portions of each of said pair of tissue engagement plates includes a generally straight edge to facilitate striking of said pair of tissue engagement plates to drive said forward bone engagement spikes into bone.

17. A device for use with a bone retractor tool comprising:
a pair of tissue engagement plates each having forward and rearward portions, each of said pair of tissue engagement plates extending generally parallel to one another wherein each of said pair of tissue engagement plates is generally rectangular in shape and generally planar and further the rearward portions of each of said pair of tissue engagement plates includes a generally straight edge to facilitate striking of said pair of tissue engagement plates to drive said forward bone engagement spikes into bone; and
forward bone engagement spikes mounted on and extending forwards from said forward portions of said pair of tissue engagement plates.

18. The device of claim 17 further comprising four forward bone engagement spikes, two mounted on each of said pair of tissue engagement plates.

* * * * *